United States Patent [19]

Hergenrother et al.

[11] Patent Number: 5,567,800

[45] Date of Patent: Oct. 22, 1996

[54] IMIDE OLIGOMERS ENDCAPPED WITH PHENYLETHYNYL PHTHALIC ANHYDRIDES AND POLYMERS THEREFROM

[75] Inventors: Paul M. Hergenrother, Yorktown; Joseph G. Smith, Jr., Grafton, both of Va.

[73] Assignee: The United States of America as represented by the Administrator of the National Aeronautics and Space Administration, Washington, D.C.

[21] Appl. No.: 330,773

[22] Filed: Oct. 28, 1994

[51] Int. Cl.[6] .......................... C08G 73/10; C08G 69/26
[52] U.S. Cl. .................. 528/353; 528/125; 528/128; 528/171; 528/172; 528/173; 528/174; 528/176; 528/183; 528/185; 528/188; 528/220; 528/229; 528/350; 528/352; 524/600; 524/606; 524/607; 525/262; 525/275; 525/282; 525/285; 428/473.5
[58] Field of Search ...................... 528/125, 128, 528/171, 172, 173, 174, 176, 183, 185, 188, 220, 229, 350, 352, 353; 524/600, 606, 607; 525/262, 285, 282, 275; 526/935; 428/473.5

[56] References Cited

U.S. PATENT DOCUMENTS

| | | | |
|---|---|---|---|
| 4,684,714 | 8/1987 | Lubowitz et al. | 528/353 |
| 5,066,771 | 11/1991 | Hino et al. | 528/353 |
| 5,138,028 | 8/1992 | Paul et al. | 528/172 |
| 5,145,937 | 9/1992 | Hergenrother et al. | 528/125 |
| 5,290,908 | 3/1994 | D'Alelio | 528/352 |
| 5,374,701 | 12/1994 | Hay et al. | 528/174 |

OTHER PUBLICATIONS

Polymer Preprints, 30(1), Apr., 1989, Siochi et al, "Model Branched Poly (methyl methacrylate)s of Controlled Molecular Weight and Architecture: Characterization", pp. 141–143.

Polymer Preprints, 30(1), Apr., 1989, DeSimone et al, "Model Branched Poly(methyl methacrylate)s of Controlled Molecular Weight and Architecture: Synthesis", pp. 137–140.

Polym. Prep. 24(2), 324–325, Aug., 1983, Harris et al "Synthesis and Characterization of Reactive End–capped Polyimids Oligomers".

J. Macromol. Sci.–Chem., A 21 (849), 1117–1135, Oct., 1984 Harris et al, "Synthesis & Characterization of Reactive End–capped Polyimide Oligomers".

Polym. Prep. 21(1), 81–83, Nov., 1980 Hergenrother, "Acetylene–terminated Imide Oligomers & Polymers Therefrom".

Polym. Prep. 34(1), 566–567, Mar., 1993, Hergenrother, "Synthesis & Properties of Phenylethynyl–terminated polyimides.".

Primary Examiner—James J. Seidleck
Assistant Examiner—P. Hampton-Hightower
Attorney, Agent, or Firm—George F. Helfrich

[57] ABSTRACT

Controlled molecular weight phenylethynyl terminated imide oligomers (PETIs) have been prepared by the cyclodehydration of precursor phenylethynyl terminated amic acid oligomers. Amino terminated amic acid oligomers are prepared from the reaction of dianhydride(s) with an excess of diamine(s) and subsequently endcapped with phenylethynyl phthalic anhydride(s) (PEPA). The polymerizations are carried out in polar aprotic solvents such as N-methyl-2-pyrrolidinone or N,N-dimethylacetamide under nitrogen at room temperature. The amic acid oligomers are subsequently cyclodehydrated either thermally or chemically to the corresponding imide oligomers. Direct preparation of PETIs from the reaction of dianhydride(s) with an excess of diamine(s) and endcapped with phenylethynyl phthalic anhydride(s) has been performed in m-cresol. Phenylethynyl phthalic anhydrides are synthesized by the palladium catalyzed reaction of phenylacetylene with bromo substituted phthalic anhydrides in triethylamine. These new materials exhibit excellent properties and are potentially useful as adhesives, coatings, films, moldings and composite matrices.

29 Claims, 2 Drawing Sheets n = ~2.5 to 25.5 ($\overline{M}_n$(calcd) = ~1500 to 12,000 g/mol)

IMIDE OLIGOMERS ENDCAPPED WITH PHENYLETHYNYL PHTHALIC ANHYDRIDES AND POLYMERS THEREFROM

ORIGIN OF INVENTION

The invention described herein was made jointly in the performance of work under NASA Grant NAG 1-1251 with Virginia Commonwealth University and an employee of the United States Government. In accordance with 35 USC 202, the grantee elected not to retain title.

BACKGROUND OF INVENTION

Polyimides (PI) are heterocyclic polymers commonly prepared by the condensation reaction of an aromatic diamine with an aromatic dianhydride or derivative thereof and having a repeat unit of the general structure

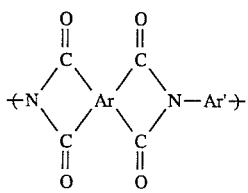

where Ar is a tetravalent aromatic radical such as 1,2,4,5-tetrasubstituted benzene. Ar may also be a bis(o-diphenylene) having the general structure

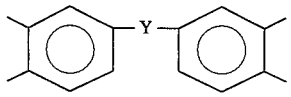

where Y=nil, O, S, $SO_2$, CO, $C(CH_3)_2$, or any other appropriate divalent radical. Ar' is a divalent aromatic radical which may be 1,3-phenylene, 1,4-phenylene, 4,4'-biphenylene, 4,4'-oxydiphenylene, 4,4'-sulfonyldiphenylene, or any other appropriate divalent radical.

The synthesis and characterization of PI has been extensively studied and documented. Reviews on PI are available. [J. W. Verbicky, Jr., "Polyimides" in Encyclopedia of Polymer Science and Engineering, $2^{nd}$ Ed., John Wiley and Sons, New York, Vol. 12, 364 (1988); C. E. Sroog, Prog. Polym. Sci., 16, 591 (1991)].

A variety of monomers, oligomers and polymers containing ethynyl (acetylenic) and substituted ethynyl (i.e. phenylethynyl) groups have been reported. The ethynyl groups in the polymer are either pendant to the chain, in the chain, or at the chain ends. Many of these materials have been used to prepare coatings, moldings, adhesives and composites [P. M. Hergenrother, "Acetylene Terminated Prepolymers" in Encyclopedia of Polymer Science and Engineering, John Wiley and Sons, New York, Vol. 1, 61 (1985)]. Good processability by either solution casting and/or compression molding has been observed for the ethynyl and substituted ethynyl containing materials. In general, thermally cured ethynyl and substituted ethynyl containing materials exhibit a favorable combination of physical and mechanical properties. Some ethynyl endcapped materials such as the Thermid® resins are commercially available (National Starch and Chemical Co., Bridgewater, N.J. 08807). Phenylethynyl containing amines have been used to terminate imide oligomers [F. W. Harris, A. Pamidimuhkala, R. Gupta, S. Das, T. Wu, and G. Mock, Polym. Prep., 24 (2), 325, 1983; F. W. Harris, A. Pamidimuhkala, R. Gupta, S. Das, T. Wu, and G. Mock, J. Macromol. Sci.-Chem., A21 (8 & 9), 1117 (1984); C. W. Paul, R. A. Schultz, and S. P. Fenelli, "High-Temperature Curing Endcaps For Polyimide Oligomers" in Advances in Polyimide Science and Technology, (Ed. C. Feger, M. M. Khoyasteh, and M. S. Htoo), Technomic Publishing Co., Inc., Lancaster, Pa., 1993, p. 220; R. G. Byrant, B. J. Jensen, and P. M. Hergenrother, Polym. Prep., 34 (1), 566, 1993]. Imide oligomers terminated with ethynyl phthalic anhydride [P. M. Hergenrother, Polym. Prep., 21 (1), 81, 1980] and substituted ethynyl phthalic acid derivatives [S. Hino, S. Sato, K. Kora, and O. Suzuki, Jpn. Kokai Tokkyo Koho JP 63, 196, 564. Aug 15, 1988; Chem. Abstr., 115573w, 110, (1989)] have been reported.

It is a primary object of the present invention to provide novel phenylethynyl phthalic anhydrides and new imide oligomers endcapped with phenylethynyl groups, as well as polymers prepared therefrom which exhibit higher elongations, higher glass transition temperatures and higher fracture toughness, as compared to similar materials.

Another object of the present invention is to provide novel polymeric materials that are useful as adhesives, coatings, films, moldings and composite matrices.

Another object of the present invention is the composition of several new phenylethynyl phthalic anhydride (PEPA) endcapping reagents.

SUMMARY OF THE INVENTION

According to the present invention the foregoing and additional objects are obtained by synthesizing controlled molecular weight imide oligomers endcapped with phenylethynyl groups by different methods. First, amino terminated amic acid (AA) oligomers are prepared by the reaction of dianhydride(s) with an excess of diamine(s) under a nitrogen atmosphere at ambient temperature in N-methyl-2-pyrrolidinone (NMP). The endcapping reagent, a phenylethynyl phthalic anhydride (PEPA), was added after the formation of the amino terminated AA oligomer. Phenylethynyl terminated amic acids have also been prepared where the PEPA endcapping reagent is added at the beginning of the reaction. The phenylethynyl terminated imide oligomers (PETI) were prepared by cyclodehydration of the precursor AA oligomers endcapped with phenylethynyl groups in NMP by azeotropic distillation with toluene. PETIs are also prepared in N,N-dimethylacetamide containing glacial acetic acid at elevated temperature. The AA oligomer can also be converted to the corresponding PETIs by treatment with chemical cyclodehydrating agents such as acetic anhydride. The direct preparation of PETIs has been performed in m-cresol containing isoquinoline at elevated temperature.

Phenylethynyl terminated imide oligomers are prepared by the reaction of the half alkyl ester of aromatic tetracarboxylic acids and the half alkyl ester of phenylethynyl substituted phthalic acids with aromatic diamines by heating in NMP. PETIs prepared by the alkyl ester route can also be prepared by heating neat or in solvents such as m-cresol. Phenylethynyl terminated imide oligomers are also prepared by the polymerization of monomeric reactants (PMR) approach by heating a mixture of a diamine and the ethyl ester derivatives of dianhydrides and phenylethynylphthalic anhydrides.

In addition, the amino terminated AA oligomer can be cyclodehydrated to the corresponding amino terminated imide and the PEPA endcapper subsequently reacted with the soluble amino terminated imide oligomer. The imide oligomer must be soluble in order to perform this endcapping reaction. Upon reaction of the amino terminated imide oligomer with the PEPA endcapper, the temperature is increased to effect cyclodehydration to complete imidization.

The inherent viscosities ($\eta_{inh}$) of the AA oligomers range from 0.16 to 0.53 dL/g. After cyclodehydration to PETIs, the $\eta_{inh}$ range from 0.12 to 0.43 dL/g. The glass transition temperatures ($T_g$) of the uncured as-isolated PETIs range from 208°–262° C. In some cases, a crystalline melt temperature is observed for the uncured PETIs. The temperature of onset and peak exotherm due to reaction of the phenylethynyl group range from 371°–414° C. and 419°–452° C., respectively as evidenced by heating in a sealed DSC pan at a heating rate of 20° C./minute. After curing at 350° C. for 1 h in a sealed DSC pan the $T_g$ of the cured polymers ranges from 237°–276° C. Thermogravimetric analysis (TGA) at a heating rate of 2.5° C./min of the uncured as-isolated PETI powders showed no weight loss occurring below 300° C. in air or nitrogen with a 5% weight loss occurring ~496° C. in air and ~512° C. in nitrogen. After a thermal cure (350° C./flowing air/1 h), TGA at a heating rate of 2.5° C./min of the cured polymers shows no weight loss occurring below 300° C. in air or nitrogen with a 5% weight loss occurring ~522° C. in air and ~525° C. in nitrogen. The average tensile strength, tensile modulus, and break elongation for inoriented thin films ranged from 15.3–20.2 ksi, 407–463 ksi, and 5–69% at 23° C.; and 8.6–12.2 ksi, 293–344 ksi, and 17–83% at 177° C., respectively. The critical stress intensity factor ($K_{1c}$) of these materials at 23° C. ranges from 2760–3529 lb√in and the critical strain energy release rate ($G_{1c}$) at 23° C. ranges from 17.7–27.4 in lb/in². The polymers prepared from these materials exhibit higher elongations, higher glass transition temperatures and higher fracture toughness as compared to similar materials.

BRIEF DESCRIPTION OF THE DRAWING

For a more complete understanding of the present invention, including its objects and attending benefits, reference should be made to the Description of the Preferred Embodiments, which is set forth in detail below. This Detailed Description should be read together with the accompanying drawing, wherein.

DESCRIPTION OF THE PREFERRED EMBODIMENTS

Figure 1:
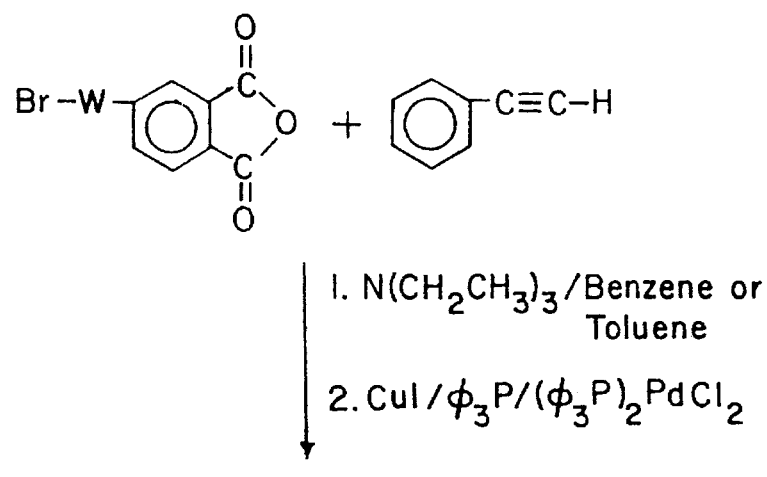
FIG. 1 is an equation showing the preparation of phenylethynyl substituted anhydrides according to the present invention.
Figure 1:
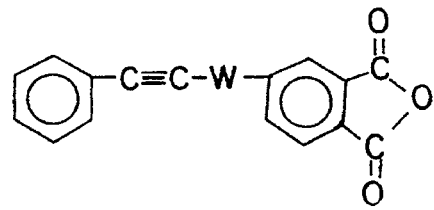
Figure 1:
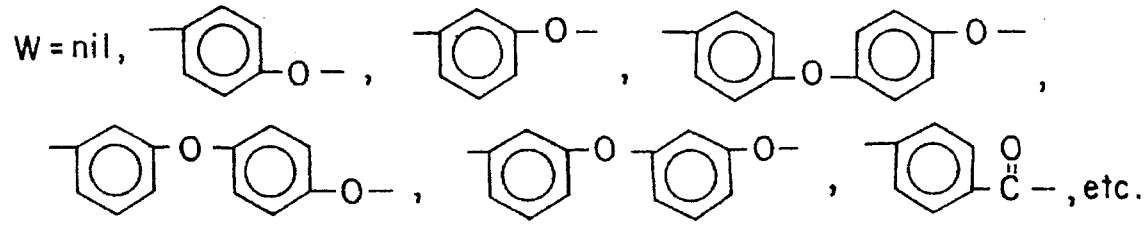
Figure 2:
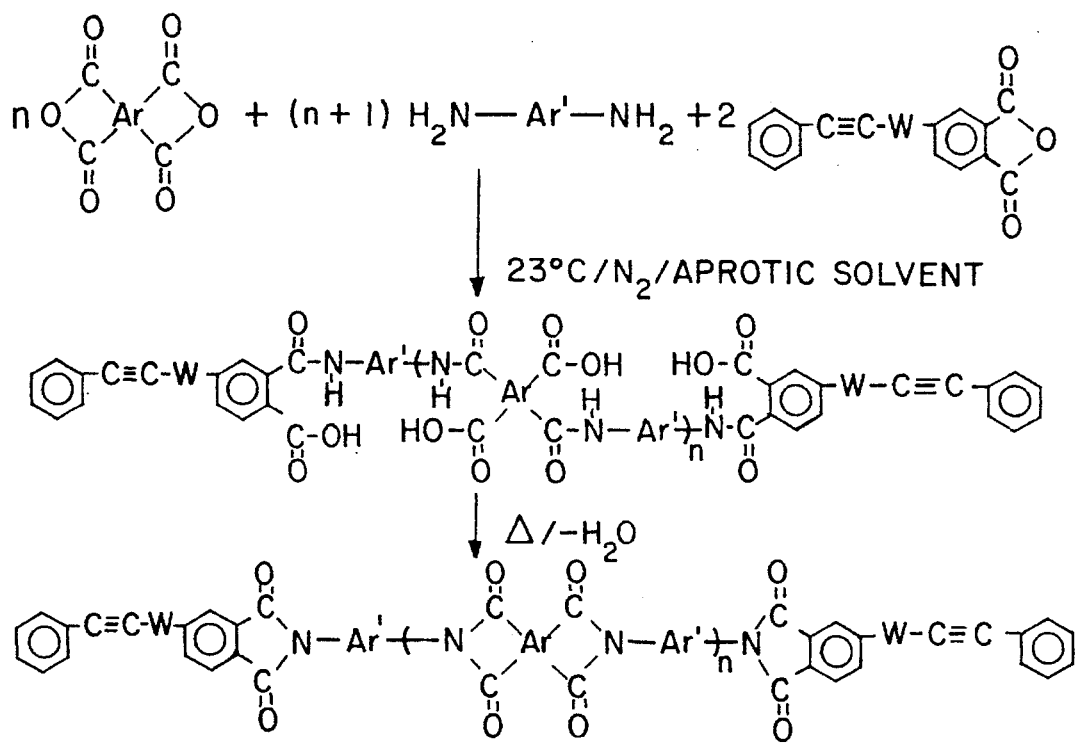
FIG. 2 is an equation showing the synthesis of controlled molecular weight phenylethynyl terminated imide oligomers (PETI) according to the present invention.
Figure 2:
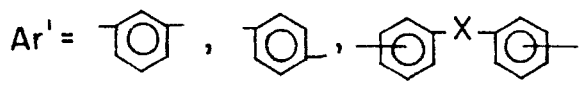
Figure 2:
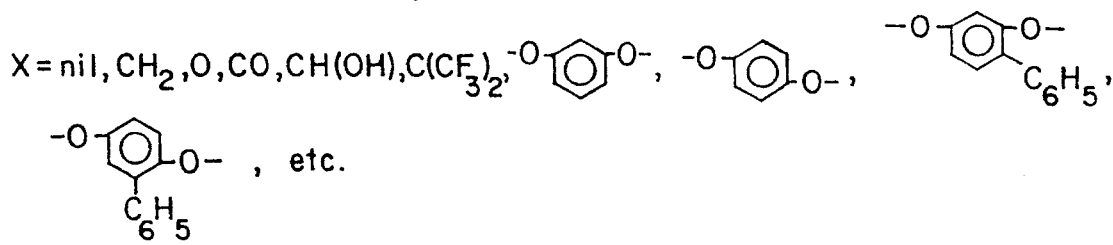
Figure 2:
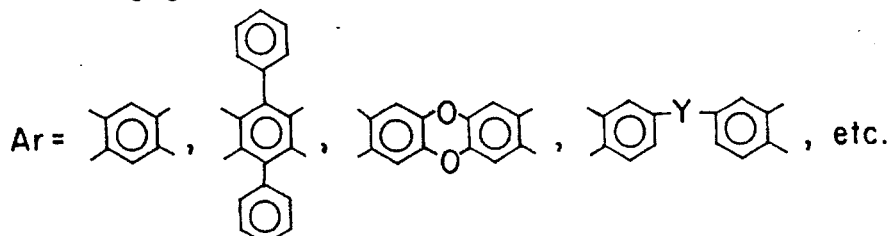
Figure 2:
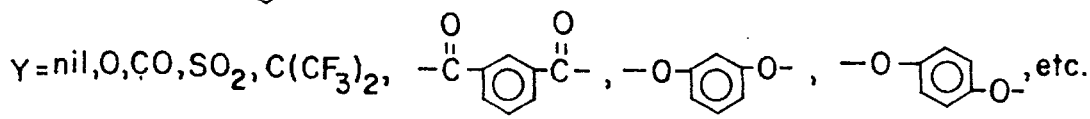
Figure 2:
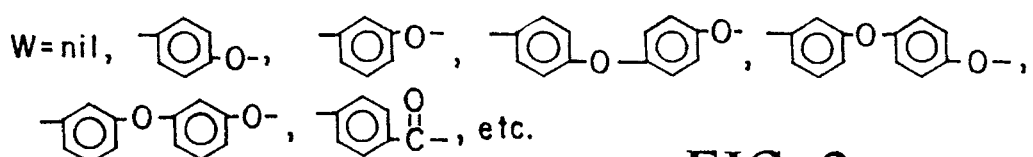

Phenylethynyl substituted phthalic anhydrides are prepared by the palladium catalyzed reaction of phenylacetylene with bromo substituted phthalic anhydrides as shown in the equation of FIG. 1. The catenation of the phenylethynyl group on the phenyl ring may be para or meta and multiple phenyl rings may have mixed connecting positions. The general reaction sequence for the synthesis of controlled molecular weight PETIs is represented in the equation of FIG. 2.

In one aspect, the present invention is a controlled molecular weight imide oligomer endcapped with phenylethynyl phthalic anhydride consisting of repeat units having the general structural formula

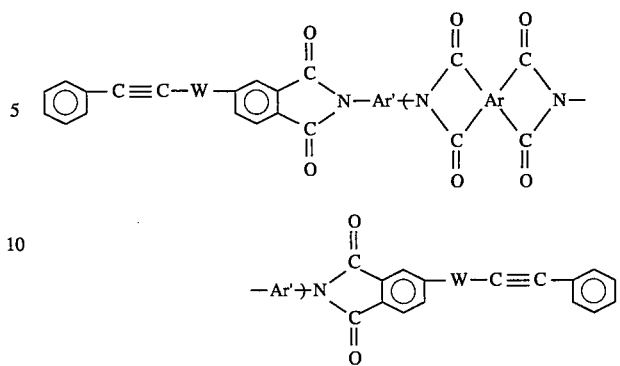

wherein Ar' is a radical selected from the group consisting of

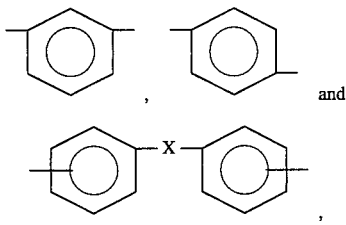

wherein the catenation is selected from the group consisting of 2,2'; 2,3'; 2,4'; 3,3'; 3,4' and 4,4', and X is a bond or X is a radical selected from the group consisting of $CH_2$, O, CO, CH(OH), $C(CF_3)_2$,

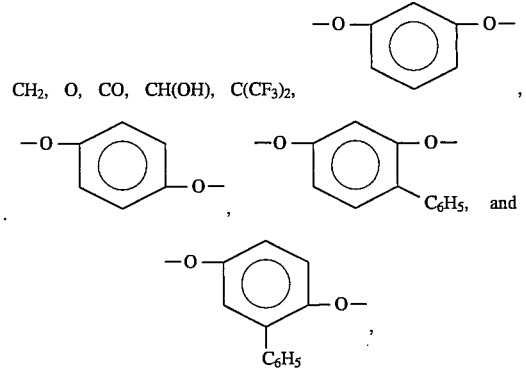

Wherein Ar is a radical selected from the group consisting of

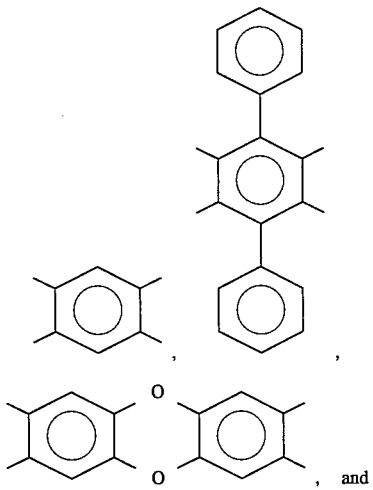

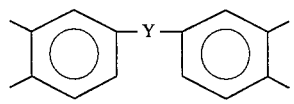

Wherein Y is a bond or Y is a radical selected from the group consisting of

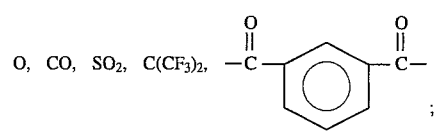

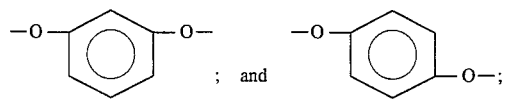

Wherein W is a bond or W is a radical selected from the group consisting of

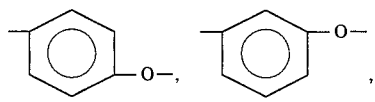

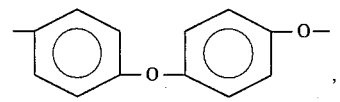

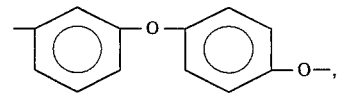

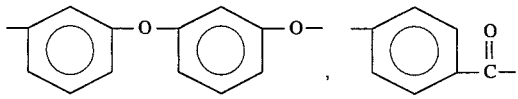

In the general structural formula above, it is especially preferred if: Ar' is a radical represented by

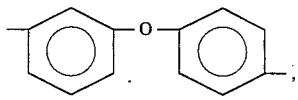

and Ar is a radical represented by

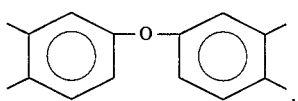

and W is a bond; Ar' is a radical represented by

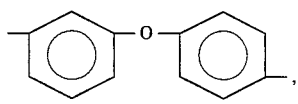

Ar is a radical represented by

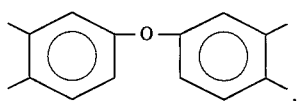

and W is a radical represented by

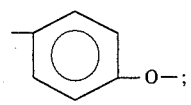

Ar' is a radical represented by

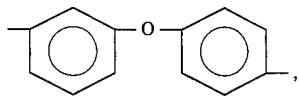

and Ar is a radical represented by

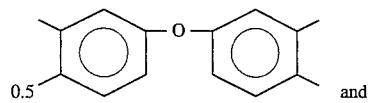

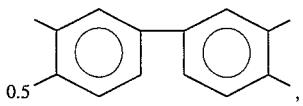

and W is a bond; Ar' is a radical represented by

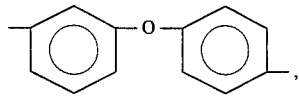

Ar is a radical represented by

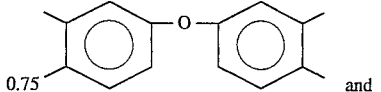

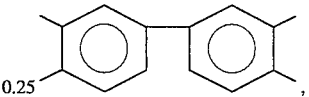

and W is a bond; Ar' is a radical represented by

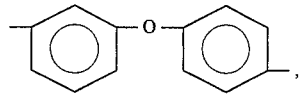

and Ar is a radical represented by

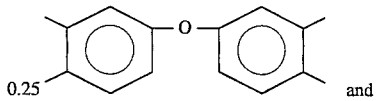

and W is a bond; Ar' is a radical represented by

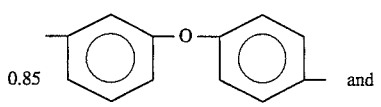

and

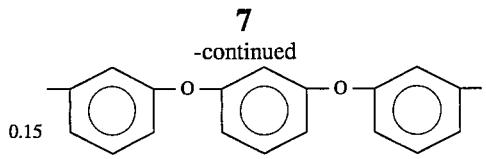

0.15

Ar is a radical represented by

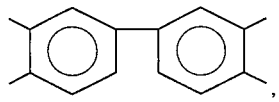

and W is a bond; Ar' is a radical represented by

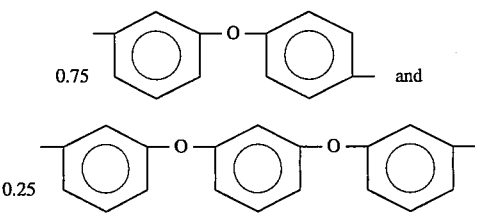

0.75   and 0.25 and Ar is a radical represented by

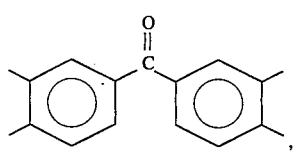

and W is a bond.

In another aspect, the present invention is a phenylethynyl phthalic anhydride having the general structural formula

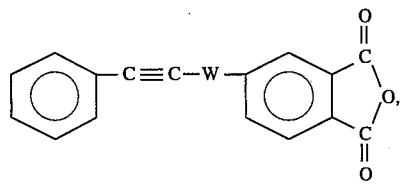

Wherein W is a radical selected from the group consisting of

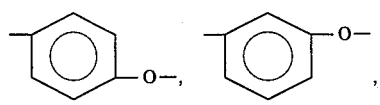

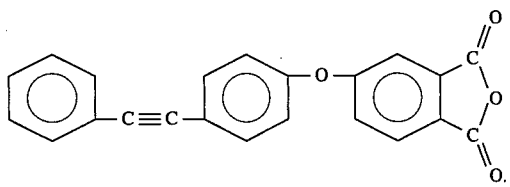

A particularly preferred phenylethynyl phthalic anhydride according to the present invention has the following structural formula:

In another aspect, the present invention is a phenylethynyl terminated amic acid oligomer having the general structural formula:

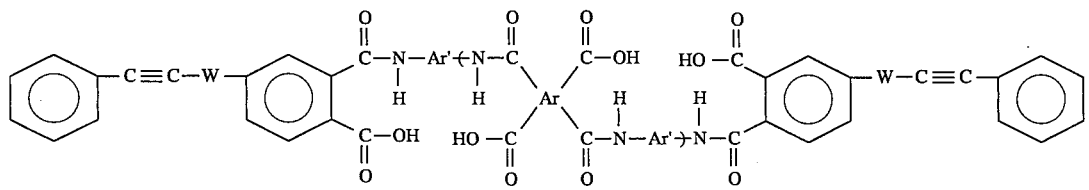

wherein Ar' is a radical selected from the group of

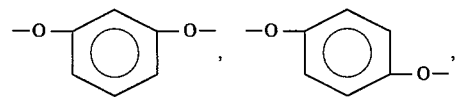

wherein the catenation is selected from the group consisting of 2,2'; 2,3'; 2,4'; 3,3'; 3,4' and 4,4' and X is bond or X is a radical selected from the group consisting of $CH_2$, O, CO, CH(OH), $C(CF_3)_2$,

Wherein Ar is a radical selected from the group consisting of

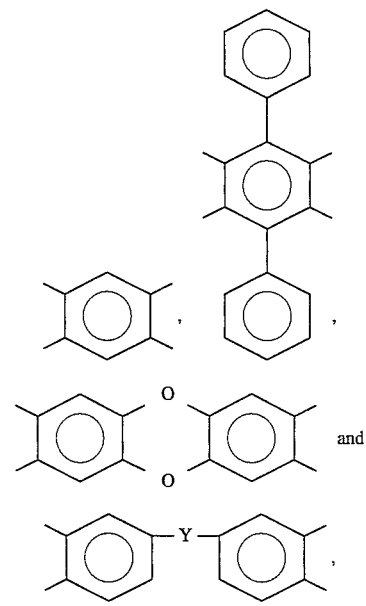

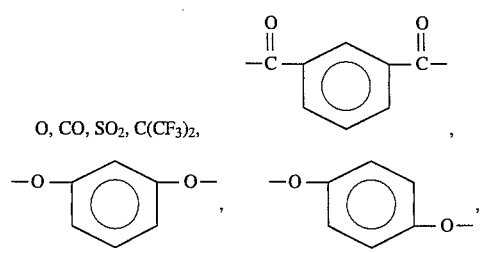 and

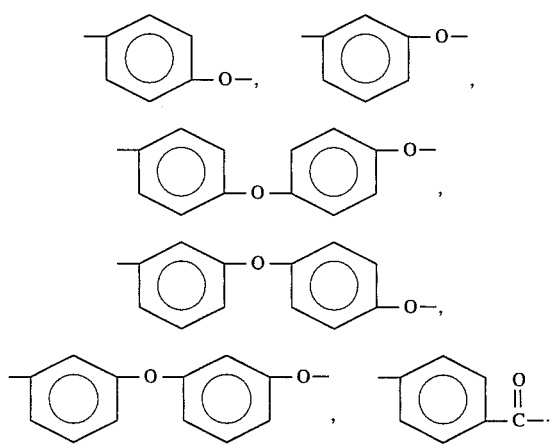

Wherein Y is a bond or Y is a radical selected from the group consisting of

O, CO, SO$_2$, C(CF$_3$)$_2$,

Wherein W is a bond or W is a radical selected from the group consisting of

Especially preferred are the following specific controlled molecular weight amic acid oligomers terminated with phenylethynyl phthalimide, reference being made to the general structural formula above. (A) wherein Ar' is a radical represented by

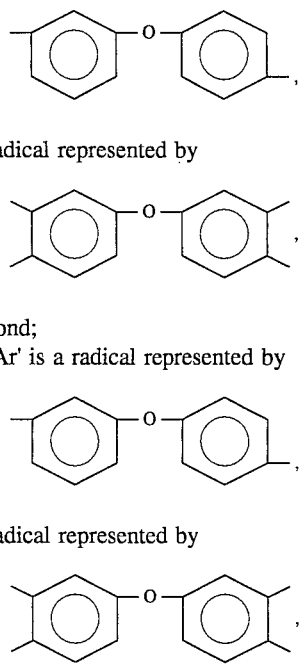

and Ar is a radical represented by and W is a bond;
(B) wherein Ar' is a radical represented by and Ar is a radical represented by and W is a radical represented by

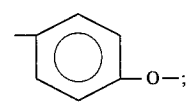

(C) wherein Ar' is a radical represented by

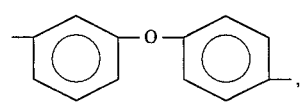

and Ar is a radical represented by

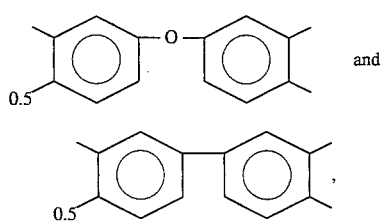 and and W is a bond;
(D) Ar' is a radical represented by

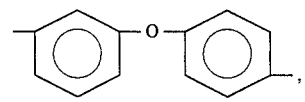,

Ar is a radical represented by

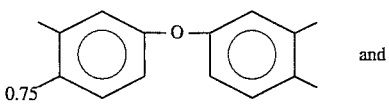 and

-continued

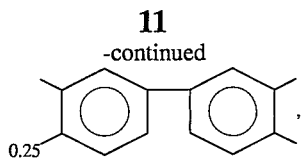

and W is a bond;

(E) Ar' is a radical represented by

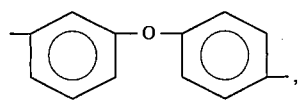

Ar is a radical represented by

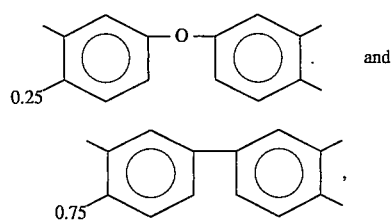

and

-and W is a bond.

In another aspect, the present invention is a process for synthesizing controlled molecular weight imide oligomers endcapped with phenylethynyl phthalimide and having the general structural formula

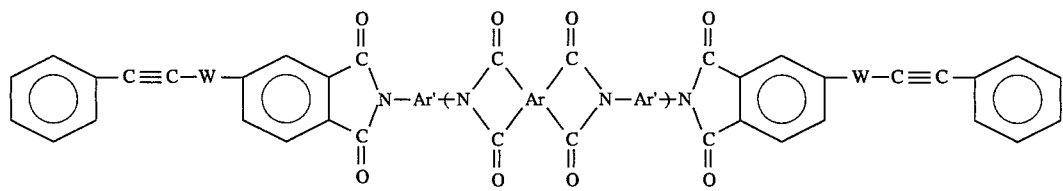

by cyclodehydration of precursor amic acid oligomers terminated with phenylethynyl phthaliamic acid and having the general structural formula

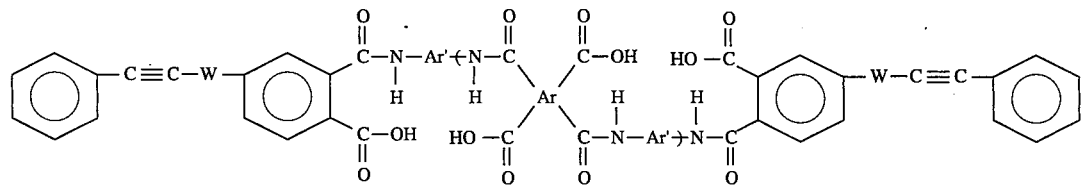

wherein the cyclodehydration reaction is carried out in a polar aprotic solvent such as N,N-dimethylacetamide, N-methyl-2-pyrrolidinone, N-cyclohexyl-2-pyrrolidinone, m-cresol, and dimethylsulfoxide; wherein the reaction is carried out with the application of heat; wherein the reaction is carried out in the presence of a member selected from the group consisting of glacial acetic acid, isoquinoline, toluene, xylenes, and wherein the reaction is carried out using acetic anhydride.

In this process, advantageous results are achieved if the phenylethynyl terminated amic acid oligomers having the general structural formula

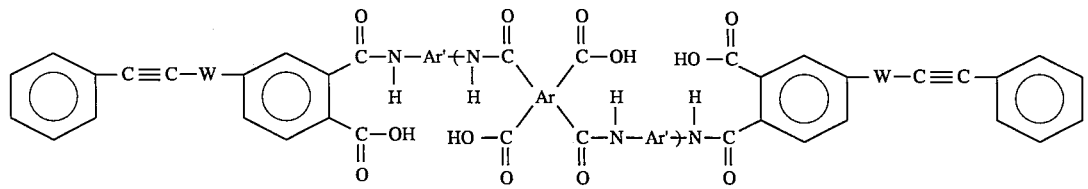

are prepared by reacting an excess of a diamine with a dianhydride and phenylethynyl phthalic anhydride.

In another aspect, the present invention is a process for synthesizing controlled molecular weight imide oligomers endcapped with phenylethynyl phthalimide by reacting an amino terminated imide oligomer with phenylethynyl phthalic anhydride to form the phenylethynyl amic acid terminated imide oligomer, wherein the reaction is carried out in a polar aprotic solvent such as N,N-dimethylacetamide, N-methyl-2-pyrrolidinone, N-cyclohexyl-2-pyrrolidinone, m-cresol, and dimethylsulfoxide; and wherein said reaction is carried out without the application of heat; followed by cyclclodehydration of the phenylethynyl amic acid terminated imide oligomer.

Especially good results are achieved if the cyclodehydration reaction is carried out in a polar aprotic solvent such as N,N-dimethylacetamide, N-methyl- 2-pyrrolidinone, N-cyclohexyl-2-pyrrolidinone, m-cresol, and dimethylsulfoxide; if the reaction is carried out with the application of heat; if the reaction is carried out in the presence of a member selected from the group consisting of glacial acetic acid, isoquinoline, toluene, xylenes, and if the reaction is carried out in the presence of acetic anyhdride.

In another aspect, the present invention is a process for synthesizing controlled molecular weight imide oligomers endcapped with phenylethynyl phthalimide by reacting a diester derivative of a dianhydride and the ester derivative of phenylethynyl phthalic anhydride with an excess of a diamine.

Very good results are obtained if the reaction is carried out in an alcohol solvent such as methanol, ethanol, isopropanol, phenol, and if the reaction is carried out with the application of heat.

In yet another aspect, the present invention is a cured film prepared from a controlled molecular weight imide oligomer endcapped by phenylethynyl phthalic anhydride. Especially good results are obtained if the film is cast from a solution of a phenylethynyl terminated amic acid oligomer as specified above wherein the solution comprises polar aprotic solvent selected from the group consisting of N,N-dimethylacetamide, N-methyl- 2-pyrrolidinone, N-cyclohexyl-2-pyrrolidinone, m-cresol, and dimethylsulfoxide, and the film is thermally cured in air or an inert atmosphere such as nitrogen, argon, or helium. Very good results are obtained if the film is prepared by compression molding of powders under heat and pressure.

In yet another aspect, the present invention is a cured neat resin molding prepared from controlled molecular weight imide oligomer endcapped by phenylethynyl phthalic anhydride. Best results are obtained when the molding is prepared under heat and pressure.

In yet another aspect, the present invention is a cured adhesive prepared from controlled molecular weight imide oligomer endcapped by phenylethynyl phthalic anhydride. Best results are achieved if the cured adhesive is prepared under heat and pressure.

In yet another aspect, the present invention is a cured composite prepared from controlled molecular weight imide oligomer endcapped with phenylethynyl phthalimide and carbon/graphite fibers. Best results are achieved if the cured composite is prepared under heat and pressure.

Having generally described the invention, a more complete understanding thereof can be obtained by reference to the following examples, which are provided herein for purposes of illustration only and do not limit the invention.

Endcapper Synthesis

The following example illustrates the reaction sequence in FIG. 1 for the preparation of the endcappers.

4-Phenylethynylphthalic Anhydride (4-PEPA)

A mixture of triethylamine (1000 ml) and benzene (120 ml) was heated to reflux for 3 h under a nitrogen atmosphere to remove any residual water. The mixture was cooled to room temperature and 4-bromophthalic anhydride (60.7462 g, 0.2676 mol), phenylacetylene (27.3314 g, 0.2676 mol), cuprous o iodide (0.1174 g, 0.6164 mmol), triphenylphosphine (0.5070 g, 1.9329 mmol), and bis(triphenylphosphine)palladium dichloride (0.1013 g, 0.1443 mmol) were added and the mixture was heated at reflux under a nitrogen atmosphere for 20 h. The cooled reaction mixture was filtered and the precipitate added to water. The crude solid was washed several times in distilled water and dried under vacuum at 85° C. for 1 h to afford 48.50 g (73% crude yield) of a brown powder mp (DSC, 10° C./min) 152° C. (sharp). The product was recrystallized from 1:1 toluene/hexanes to afford 41.30 g (62% yield) of an orange-brown crystalline solid, mp (DSC, 10° C./min) 151° C. (sharp). An exotherm with a peak of 389° C. had a ΔH of 390 J/g. IR (KBr): 2206 cm$^{-}$(—C≡C—); 1843 cm$^-$and 1771 cm$^{-1}$(asymmetric and symmetric C=O stretch). Anal. calcd. for $C_{16}H_8O_3$: C, 77.42%; H, 3.14%; Found: C, 77.12%; H, 3.14%. Mass spectroscopy: m/e 248 (calcd. molecular weight: 248.2414 g/mol).

4-(4-Bromophenoxy)phthalic Anhydride

A mixture of 4-bromophenol (21.7029 g, 0.1254 mol), 4-fluorophthalic anhydride (22.9027 g, 0.1379 mol), and potassium fluoride (11.1003 g, 0.1911 mol) in sulfolane (142.34 g, 21.95% w/w) was heated at 165°–170° C. for 10.5 h. The cooled light brown mixture was precipitated in water and the solid collected by filtration. The crude solid was subsequently washed in water and dried under vacuum at 75° C. to afford 35.1 g (88% crude yield) of a pink-orange powder, mp (DSC, 10° C./min)=104° C. (broad). The crude product was recrystallized from 2.6:1 cyclohexane/benzene to afford 26.97 g (67% yield) of a light orange powder, mp (DSC, 10° C./min)=106° C. (sharp). IR (KBr): 1843 cm$^-$and 1767 cm$^{-1}$ (asymmetric and symmetric C=O stretch). Anal. calcd. for $C_{14}H_7O_4Br$: C, 52.69%; H, 2.21%; Br, 25.04%; Found: C, 52.09%; H, 2.23%; Br, 25.32%. Mass spectroscopy: m/e 319.9 (calcd. molecular weight: 319.1194 g/mol).

4-(4-Phenylethynylphenoxy)phthalic Anhydride (4-PEPOPA)

A mixture of triethylamine (600 ml) and benzene (100 ml) was heated to reflux for 3 h under a nitrogen atmosphere to remove any residual water. The mixture was cooled to room temperature and 4-(4-bromophenoxy)phthalic anhydride (26.0078 g, 0.0815 mol), phenylacetylene (8.3230 g, 0.0815 mol), cuprous iodide (0.1111 g, 0.5834 mmol), triphenylphosphine (0.5493 g, 2.0942 mmol), and bis(triphenylphosphine) palladium dichloride (0.1208 g, 0.1721 mmol) were added and the mixture was heated at reflux under a nitrogen atmosphere for 24 h. The cooled reaction mixture was filtered and the precipitate added to water. The crude solid was washed several times in distilled water and dried under vacuum at 115° C. for 3 h to afford 10.49 g (33% crude yield) of a brown powder, mp (DSC, 10° C./min) 199° C. (broad). The crude product was recrystallized from 1:1 toluene/hexane and dried at 105° C. under vacuum for 2 h to afford 8.03 g (29% yield) of a yellow-tan powder, mp (DSC, 20° C./min) 202° C. (broad). An exotherm with a peak of 420° C. had a ΔH of 120 J/g. IR (KBr): 1853 cm$^{-1}$ and 1765 cm$^{-1}$ (asymmetric and symmetric C=O stretch).

Anal. calcd. for $C_{22}H_{12}O_4$: C, 77.64%; H, 3.55%; Found: C, 76.80%; H, 3.66%. Mass spectroscopy: m/e 339.9 (calcd. molecular weight: 340.3400 g/mol).

Imide Oligomers Endcapped With Phenylethynyl Phthalic Anhydrides

Example 1

3,4'-Oxydianiline and 4,4'-Oxydiphthalic Anhydride, Using 5 mole % Stoichiometric offset and 10 mole % 4-Phenylethynylphthalic Anhydride The following example illustrates the reaction sequence in FIG. 2 for the preparation of the controlled molecular weight PETI where Ar' is equal to a diphenylene where X is an oxygen atom located in the 3,4'-position, Ar is equal to a bis(o-diphenylene) where Y is an oxygen atom located in the 4,4'-position, and where W is equal to a nil group. The stoichiometric imbalance is 5 mole % and the endcapping reagent is 10 mole % of 4-phenylethynylphthalic anhydride.

Into a flame dried 250 ml three necked round bottom flask equipped with nitrogen inlet, thermometer, mechanical stirrer, and drying tube were placed 3,4'-oxydianiline (6.753 g, 0.0337 mol) and 50 ml (12.5% w/w) of N,N'-dimethylacetamide (DMAc). After dissolution, 4,4'-oxydiphthalic anhydride (9.9389 g, 0.0320 mol) and 45 ml of DMAc (15.7% w/w) were added. The solution was allowed to stir for ~.8 h at room temperature under a nitrogen atmosphere. 4-Phenylethynylphthalic anhydride (0.8372 g, 0.0034 mol) and 3 ml of DMAc (16.0% w/w) were added and the reaction stirred at room temperature for an additional 16 h. The inherent viscosity of the amic acid oligomeric solution (0.5% in DMAc at 25° C.) was 0.36 dL/g. Glacial acetic acid (9 ml) was added to the solution and the temperature increased and maintained at ~120° C. for ~16 h under a nitrogen atmosphere. As cyclodehydration to the imide occurred, a precipitate formed. The mixture was cooled, the isolated precipitate was washed with hot water and warm methanol, and dried under vacuum at 160° C. for 5 h to provide a tan powder (15.2 g, 93% yield). The inherent viscosity of a 0.5% solution in m-cresol at 25° C. was 0.12 dL/g. The $T_g$ of the uncured as-isolated oligomer was not apparent on the initial DSC scan, but $T_m$s were observed (DSC, 20° C./min) at 254°, 285°, and 31 5° C. with an exothermic onset and peak at 394° C. and 434° C., respectively. The $T_g$ of the cured polymer (cure conditions: 350° C./1 h/flowing air) was 248° C. Unoriented thin films cast from a DMAc solution of the amic acid oligomer and cured at 100°, 225°, and 350° C. for 1 h each in flowing air gave tensile strength, tensile modulus, and elongation at break at 23° C. of 17.3 ksi, 413 ksi, and 38% and at 177° C. of 9.4 ksi, 318 ksi, and 60%, respectively. The $T_g$ of the cured film was 251° C.

Example 2

3,4'-Oxydianiline and 4,4'-Oxydiphthalic Anhydride, Using 5.14 mole % Stoichiometric offset and 10.28 mole % 4-Phenylethynylphthalic Anhydride The following example illustrates the reaction sequence in FIG. 2 for the preparation of the controlled molecular weight PETI where Ar' is equal to a diphenylene where X is an oxygen atom located in the 3,4'-position, Ar is equal to a bis(o-diphenylene) where Y is an oxygen atom located in the 4,4'-position, and where W is equal to a nil group. The stoichiometric imbalance is 5.14 mole % and the endcapping reagent is 10.28 mole % of 4-phenylethynylphthalic anhydride.

Into a flame dried 250 ml three necked round bottom flask equipped with nitrogen inlet, thermometer, mechanical stirrer, and drying tube were placed 3,4'-oxydianiline (8.4413 g, 0.0422 mol) and 50 ml (14.0% w/w) N-methyl-2-pyrrolidinone (NMP). After dissolution, 4,4'-oxydiphthalic anhydride (12.4053 g, 0.0400 mol) and 50 ml of NMP (16.8% w/w) were added. The solution was allowed to stir for ~8 h at room temperature under a nitrogen atmosphere. 4-Phenylethynylphthalic anhydride (1.0758 g, 0.0043 mol) and 10 ml NMP (16.2% w/w) were added and the reaction stirred at room temperature for an additional 16 h. The inherent viscosity of the amic acid oligomeric solution (0.5% in NMP at 25° C.) was 0.38 dL/g. Toluene (70 ml) was added to the amic acid oligomeric solution and the temperature increased and maintained at ~150° C. for ~16 h under a nitrogen atmosphere. As cyclodehydration to the imide occurred, a precipitate formed. The mixture was cooled, the oligomer was washed in hot water, warm methanol, and dried under vacuum at 160° C. for 5 h to provide an off-white powder (19.46 g, 97% yield). The inherent viscosity of a 0.5% solution of the imide oligomer in m-cresol at 25° C. was 0.29 dL/g. The $T_g$ of the uncured as-isolated oligomer (DSC, 20° C./min) was 236° C., $T_m$ was 323° C. and the exothermic onset and peak occurred at 397° C. and 442° C., respectively. The $T_g$ of the cured polymer (cure conditions: 350° C./1 h/static air) was 243° C.

Example 3

3,4'-Oxydianiline and 4,4'-Oxydiphthalic Anhydride, Using 5.14 mole % Stoichiometric offset and 10.28 mole % 4-Phenylethynylphthalic Anhydride The following example illustrates the reaction sequence in FIG. 2 for the preparation of the controlled molecular weight PETI where Ar' is equal to a diphenylene where X is an oxygen atom located in the 3,4'-position, Ar is equal to a bis(o-diphenylene) where Y is an oxygen atom located in the 4,4'-position, and where W is equal to a nil group. The stoichiometric imbalance is 5.14 mole % and the endcapping reagent is 10.28 mole % of 4-phenylethynylphthalic anhydride.

Into a flame dried 250 ml three necked round bottom flask equipped with nitrogen inlet, thermometer, mechanical stirrer, and drying tube were placed 3,4'-oxydianiline (8.4413 g, 0.0422 mol) and 50 ml (14.0% w/w) of m-cresol. After dissolution, 4,4'-oxydiphthalic anhydride (12.4053 g, 0.0400 mol), 4-phenylethynylphthalic anhydride (1.0758 g, 0.0043 mol) and 60 ml of m-cresol (15.0% w/w) were added and the reaction stirred at room temperature for ~16 h. Isoquinoline (5 drops) was added to the mixture. The temperature was increased and maintained at ~200° C. for ~6.5 h under a nitrogen atmosphere. The mixture was cooled, the oligomer precipitated in methanol, washed in warm methanol, and dried at 150° C. under vacuum for 5 h to provide an off-white powder (20.0 g, 100% yield). The inherent viscosity of a 0.5% solution of the imide oligomer in m-cresol at 25° C. was 0.29 dL/g and in NMP at 25° C. was 0.33 dug. The $T_g$ of the uncured as-isolated oligomer (DSC, 20° C./min) was 219° C. with an exothermic onset and peak at 371° C. and 425° C., respectively. The $T_g$ of the cured polymer (cure conditions: 350° C./1 h/flowing air) was 246° C. A sample compression molded at 350° C./200 psi/1h had

Example 4

3,4'-Oxydianiline and 4,4'-Oxydiphthalic Anhydride, Using 5.14 mole % Stoichiometric offset and 10.28 mole % 4-Phenylethynylphthalic Anhydride The following example illustrates the reaction sequence in FIG. 2 for the preparation of the controlled molecular weight PETI where Ar' is equal to a diphenylene where X is an oxygen atom located in the 3,4'-position, Ar is equal to a bis(o-diphenylene) where Y is an oxygen atom located in the 4,4'-position, and where W is equal to a nil group. The stoichiometric imbalance is 5.14 mole % and the endcapping reagent is 10.28 mole % of 4-phenylethynylphthalic anhydride.

Into a 250 ml three necked round bottom flask equipped with nitrogen inlet, thermometer, mechanical stirrer, and condensor were placed 4,4'-oxydiphthalic anhydride (18.6081 g, 0.0600 mol), 4-phenylethynylphthalic anhydride (1.6137 g, 0.0065 mol), and 130 ml absolute ethanol. The mixture was brought to reflux and maintained for ~4.5 h. As the anhydrides were converted to the corresponding ester derivatives, the solution cleared. To the cooled solution was added 3,4'-oxydianiline (12.6620 g, 0.0632 mol) and 50 ml absolute ethanol and the mixture stirred for ~16 h at room temperature under a nitrogen atmosphere. Approximately 92 g of solution was decanted and the solvent evaporated. To the remaining solution was added 80 ml NMP and the temperature increased and maintained at ~170° C. for ~20 h. As cyclodehydration to the imide occurred, a precipitate formed. The mixture was cooled, the oligomer was washed in hot water, warm methanol, and dried under vacuum at 240° C. for 4 h to provide a brown powder (11.90 g). The $T_g$ of the uncured as-isolated oligomer (DSC, 20° C./min) was 226° C. and $T_m$s at 274°, 303°, and 325° C. The $T_g$ of the cured polymer (cure conditions: 350° C./1 h/DSC pan) was 241° C. The ethanol solution of monomers was evaporated to afford 21.93 g of a brown powder. The uncured as-isolated monomers (DSC, 20° C./min) exhibited endothermic melts at 124°, 132°, 144°, and 155° C. The $T_g$ of the cured polymer (cure conditions: 350° C./1 h/DSC pan) was 235° C.

Example 5

3,4'-Oxydianiline and 4,4'-Oxydiphthalic Anhydride, Using 5.14 mole % Stoichiometric offset and 10.28 mole % 4-(4-Phenylethynylphenoxy)phthalic Anhydride The following example illustrates the reaction sequence in FIG. 2 for the preparation of the controlled molecular weight PETI where Ar' is equal to a diphenylene where X is an oxygen atom located in the 3,4'-position, Ar is equal to a bis(o-diphenylene) where Y is an oxygen atom located in the 4,4'-position, and where W is equal to a 4-phenoxy group. The stoichiometric imbalance is 5.14 mole % and the endcapping reagent is 10.28 mole% of 4-(4-phenylethynylphenoxy)phthalic anhydride.

Into a flame dried 300 ml three necked round bottom flask equipped with nitrogen inlet, thermometer, mechanical stirrer, and drying tube were placed 3,4'-oxydianiline (7.2371 g, 0.0361 mol) and 50 ml (12.3% w/w) N-methyl-2-pyrrolidinone (NMP). After dissolution, 4,4'-oxydiphthalic anhydride (10.6358 g, 0.0343 mol), 4-(4-phenylethynylphenoxy)phthalic anhydride (1.2645 g, 0.0037 mol) and 45 ml NMP (14.9% w/w) were added and the reaction stirred at room temperature for 24 h. The inherent viscosity of the amic acid oligomeric solution (0.5% in NMP at 25° C.) was 0.53 dL/g. Approximately 30 g of amic acid oligomeric solution was used to cast an unoriented thin film. Toluene (70 ml) was added to the remaining amic acid oligomeric solution and the temperature increased and maintained at ~150° C. for ~16 h under a nitrogen atmosphere. As cyclodehydration to the imide occurred, a precipitate formed. The mixture was cooled, the oligomer was washed in hot water, warm methanol, and dried under vacuum at 210° C. for 3 h to provide an off-white powder (13.05 g, 100% yield). The $T_g$ of the uncured as-isolated oligomer (DSC, 20° C./min) was 216° C., $T_m$s were 273 and 323° C. and the exothermic onset and peak occurred at 414° C. and 452° C., respectively. The $T_g$ of the cured polymer (cure conditions: 350° C./1 h/static air) was 246° C. Unoriented thin films cast from a NMP solution of the amic acid oligomer cured at 100°, 225°, and 350° C. for 1 h each in flowing air gave tensile strength, tensile modulus, and elongation at break at 23° C. of 16.9 ksi, 408 ksi, and 35% and at 177° C. of 8.6 ksi, 293 ksi, and 56%, respectively. The $T_g$ of the cured film was 247° C. A sample compression molded at 350° C./200 psi/1h had a $G_{1C}$ (critical strain energy release rate) of 25.7 in lb/in$^2$.

Mixtures of dianhydrides have been used to alter properties as illustrated in Examples 6 and 7.

Example 6

3,4'-Oxydianiline and 1:1 4,4'-Oxydiphthalic Anhydride, and 3,3',4,4'-Biphenyl Tetracarboxylic Dianhydride, Using 5.14 mole % Stoichiometric offset and 10.28 mole % 4-Phenylethynylphthalic Anhydride The following example illustrates the reaction sequence in FIG. 2 for the preparation of the controlled molecular weight PETI where Ar' is equal to a diphenylene where X is an oxygen atom located in the 3,4'-position; Ar (1) is equal to a bis(o-diphenylene) where Y is an oxygen atom located in the 4,4'-position and Ar (2) is equal to a bis(o-diphenylene) where Y is a nil group located in the 4,4'-position, and where W is equal to a nil group. The ratio of dianhydrides [Ar (1):Ar (2)] is 1:1. The stoichiometric imbalance is 5.14 mole % and the endcapping reagent is 10.28 mole % of 4-phenylethynylphthalic anhydride.

Into a flame dried 500 ml three necked round bottom flask equipped with nitrogen inlet, thermometer, mechanical stirrer, and drying tube were placed 3,4'-oxydianiline (17.1723 g, 0.0858 mol) and 100 ml of NMP (14.3% w/w). After dissolution, 4,4'-oxydiphthalic anhydride (12.6288 g, 0.0407 mol) and 3,3',4,4'-biphenyl tetracarboxylic dianhydride (11.9775 g, 0.0407 mol) and 100 ml of NMP (16.8% w/w) were added and the solution stirred for ~8 h at room temperature under a nitrogen atmosphere. 4-Phenylethynylphthalic anhydride (2.1501 g, 0.0087 mol) and 15 ml of NMP (16.5% w/w) were added and the reaction stirred at room temperature for an additional 16 h. The inherent viscosity of the amic acid oligomeric solution (0.5% in NMP at 25° C.) was 0.43 dL/g. Approximately 30 g of amic acid oligomeric solution was used to cast an unoriented thin film. Toluene (100 ml) was added to the remaining amic acid oligomeric solution and the temperature increased and maintained at ~150° C. for ~16 h under a nitrogen atmosphere. As the amic acid oligomer was cyclodehydrated to the imide, the imide oligomer remained in solution. The solution was heated for an additional 5 h at ~175° C. under a nitrogen atmosphere. The mixture was cooled, the polymer precipitated in water, washed in hot water, warm methanol, and dried under vacuum at 160° C. for 3 h to provide an off-white powder (35.10 g, 88% yield). The inherent viscosity of a 0.5% solution of the imide oligomer in NMP at 25° C. was 0.38 dL/g. The $T_g$ of the uncured as-isolated imide oligomer (DSC, 20° C./min) was 239° C. with an exothermic onset and peak at 377° C. and 436° C., respectively. The $T_g$ of the cured polymer (cure conditions: 350° C./1 h/static air) was 263° C. Unoriented thin films cast from a NMP solution of the amic acid oligomer cured at 100°, 225°, and 350° C. for 1 h each in flowing air gave tensile strength, tensile modulus, and elongation at break at 23° C. of 20.2 ksi, 431 ksi, and 69% and at 177° C. of 10.7 ksi, 341 ksi, and 70%, respectively. The $T_g$ of the cured film was 262° C. A sample compression molded at 350° C./200 psi/1h had a $G_{1C}$ (critical strain energy release rate) of 17.68 in lb/in$^2$ and a $T_g$ of 248° C.

Example 7

3,4'-Oxydianiline and 1:14,4'-Oxydiphthalic Anhydride, and 3,3',4,4'-Biphenyl Tetracarboxylic Dianhydride, Using 7.635 mole % Stoichiometric offset and 15.27 mole % 4-Phenylethynylphthalic Anhydride The following example illustrates the reaction sequence in FIG. 2 for the preparation of the controlled molecular weight PETI where Ar' is equal to a o diphenylene where X is an oxygen atom located in the 3,4'-position; Ar (1) is equal to a bis(o-diphenylene) where Y is an oxygen atom located in the 4,4'-position and Ar (2) is equal to a bis(o-diphenylene) where Y is a nil group located in the 4,4'-position, and where W is equal to a nil group. The ratio of dianhydrides [Ar (1):Ar (2)] is 1:1. The stoichiometric imbalance is 7.635 mole % and the endcapping reagent is 15.27 mole % of 4-phenylethynylphthalic anhydride.

Into a flame dried 500 ml three necked round bottom flask equipped with nitrogen inlet, thermometer, mechanical stirrer, and drying tube were placed 3,4'-oxydianiline (18.0309 g, 0.0900 mol) and 100 ml of NMP (14.9% w/w). After dissolution, 4,4'-oxydiphthalic anhydride (12.9223 g, 0.0417 mol) and 3,3',4,4'-biphenyl tetracarboxylic dianhydride (12.2558 g, 0.0417 mol) and 100 ml of NMP (17.3% w/w) were added and the solution stirred for ~8 h at room temperature under a nitrogen atmosphere. 4-Phenylethynylphthalic anhydride (3.3440 g, 0.0135 mol) and 50 ml of NMP (15.3% w/w) were added and the reaction stirred at room temperature for an additional 16 h. The inherent viscosity of the amic acid oligomeric solution (0.5% in NMP at 25° C.) was 0.32 dL/g. Approximately 28 g of amic acid oligomeric solution was used to cast an unoriented thin film. Toluene (100 ml) was added to the remaining amic acid oligomeric solution and the temperature increased and maintained at ~160° C. for ~24 h under a nitrogen atmosphere. As the amic acid oligomer was cyclodehydrated to the imide, the imide oligomer remained in solution. The mixture was cooled, the polymer precipitated in water, washed in hot water, warm methanol, and dried under vacuum at 150° C. for 3.5 h to provide an off white powder (39.4 g, 94% yield). The inherent viscosity of a 0.5% solution of the imide oligomer in NMP at 25° C. was 0.32 dL/g. The $T_g$ of the uncured as-isolated imide oligomer (DSC, 20° C./min) was 222° C. with an exothermic onset and peak at 372° C. and 419° C., respectively. The $T_g$ of the cured polymer (cure conditions: 350° C./1 h/static air) was 267° C. Unoriented thin films cast from a NMP solution of the amic acid oligomer cured at 100°, 225°, and 350° C. for 1 h each in flowing air gave tensile strength, tensile modulus, and elongation at break at 23° C. of 17.9 ksi, 427 ksi, and 40% and at 177° C. of 10.8 ksi, 344 ksi, and 63%, respectively. The $T_g$ of the cured film was 268° C.

Mixtures of diamines have been used to alter properties as illustrated in Examples 8 and 9.

Example 8

0.85:0.15 3,4'-Oxydianiline and 1,3-bis(3-aminophenoxy)benzene, and 3,3',4,4'-Biphenyl Tetracarboxylic Dianhydride, Using 9.02 mole % Stoichiometric offset and 18.04 mole % 4-Phenylethynylphthalic Anhydride The following example illustrates the reaction sequence in FIG. 2 for the preparation of the controlled molecular weight PETI where Ar' (1) is equal to a diphenylene where X is an oxygen atom located in the 3,4'-position and Ar' (2) is equal to a diphenylene where X is a 1,3-dioxybenzene and Ar is equal to a bis(o-diphenylene) where Y is a nil group located in the 4,4'-position, and where W is equal to a nil group. The ratio of diamines [Ar' (1):Ar' (2)] is 0.85:0.15. The stoichiometric imbalance is 9.02 mole % and the endcapping reagent is 18.04 mole % of 4-phenylethynylphthalic anhydride.

Into a flame dried 250 ml three necked round bottom flask equipped with nitrogen inlet, thermometer, mechanical stirrer, and drying tube were placed 3,4'-oxydianiline (10.8126 g, 0.0540 mol), 1,3-bis(3-aminophenoxy)benzene (2.7857 g, 0.0095 mol) and 90 ml of NMP (12.8% w/w). After dissolution, 3,3',4,4'-biphenyl tetracarboxylic dianhydride (17.0049 g, 0.0578 mol), 4-phenylethynylphthalic anhydride (2.8449 g, 0.0115 mol) and 90 ml of NMP (15.3% w/w) were added and the reaction stirred at room temperature for 20 h. The inherent viscosity of the amic acid oligomeric solution (0.5% in NMP at 25° C.) was 0.27 dL/g. Approximately 25 g of amic acid oligomeric solution was used to cast an unoriented thin film. Toluene (70 ml) was added to the remaining amic acid oligomeric solution and the temperature increased and maintained at ~180° C. for ~24 h under a nitrogen atmosphere. As the amic acid oligomer was cyclodehydrated to the imide, a precipitate formed. The mixture was cooled, the oligomer washed in hot water, warm methanol, and dried under vacuum at 240° C. for 4 h to provide a yellow powder (24.2 g, 78% yield). The inherent viscosity of a 0.5% solution of the imide oligomer in m-cresol at 25° C. was 0.28 dL/g. The $T_g$ of the uncured as-isolated oligomer (DSC, 20° C./min) was 208° C. and the $T_g$ was 288° C. The $T_m$ of the cured polymer (cure conditions: 350° C./1 h/static air) was 249° C. Unoriented thin films cast from a NMP solution of the amic acid oligomer cured at 100°, 225°, and 350° C. for 1 h each in flowing air gave tensile strength, tensile modulus, and elongation at break at 23° C. of 18.8 ksi, 455 ksi, and 32% and at 177° C. of 12.2 ksi, 332 ksi, and 83%, respectively. The $T_g$ of the cured film was 270° C. A sample compression molded at 350° C./150 psi/1h had a $G_{1C}$ (critical strain energy release rate) of 27.4 in lb/in$^2$.

Example 9

0.75:0.25 3,4'-Oxydianiline and 1,3-bis(3-aminopbenoxy)benzene, and 3,3',4,4'-Benzophenone Tetracarboxylic Dianhydride, Using 29.03 mole % Stoichiometric offset and 58.06 mole % 4-Phenylethynylphthalic Anhydride The following example illustrates the reaction sequence in FIG. 2 for the preparation of the controlled molecular weight PETI where Ar' (1) is equal to a diphenylene where X is an oxygen atom located in the 3,4'-position and Ar' (2) is equal to a diphenylene where X is a 1,3-dioxybenzene and Ar is equal to a bis(o-diphenylene) where Y is a carbonyl group located in the 4,4'-position, and where W is equal to a nil group. The ratio of diamines [Ar' (1):Ar' (2)] is 0.75:0.25. The stoichiometric imbalance is 29.03 mole % and the endcapping reagent is 58.06 mole % of 4-phenylethynylphthalic anhydride.

Into a flame dried 250 ml three necked round bottom flask equipped with nitrogen inlet, thermometer, mechanical stirrer, and drying tube were placed 3,4'-oxydianiline (10.5323 g, 0.0526 mol), 1,3-bis(3-aminophenoxy)benzene (5.1256 g, 0.0175 mol) and 25 ml of NMP (37.8% w/w). After dissolution, a slurry of 3,3',4,4'-benzophenone tetracarboxylic dianhydride (16.0382 g, s 0.0498 mol) and 4-phenylethynylphthalic anhydride (10.1079 g, 0.0407 mol) in 50 ml of NMP (33.6% w/w) were added to the stirred solution. An additional 45 ml of NMP was used to rinse in the anhydrides. The solids content was 25.2% w/w (120 ml total NMP). The mixture was stirred overnight at room temperature under nitrogen. The inherent viscosity of the amic acid oligomeric solution (0.5% in NMP at 25° C.) was 0.16 dL/g. Toluene (70 ml) was added to the amic acid oligomeric solution and the temperature increased and maintained at ~180° C. for ~24 h under a nitrogen atmosphere. As the amic acid oligomer was cyclodehydrated to the imide, a precipitate formed. The mixture was cooled, the oligomer washed in hot water, warm methanol, and dried under vacuum at 240° C. for 4 h to provide a yellow powder (38.4 g, 98% yield). The $T_g$ of the uncured as-isolated oligomer (DSC, 20° C./min) was 262° C. and the $T_m$ was 341° C. The $T_g$ of the cured polymer (cure conditions: 3600C/1 h/static air) was 276° C.

In the tables which follow, oligomer and polymer characterization is presented in Table 1; unoriented thin film properties are presented in Table 2; adhesive properties are presented in Table 3; and composite properties are presented in Table 4.

TABLE 1

| | | | | | | | |
|---|---|---|---|---|---|---|---|
| | | \multicolumn{6}{c}{OLIGOMER and POLYMER CHARACTERIZATION} | | | | | | |
| Imide No.[1] | Calc'd ($M_n$) g/mol | $\eta_{inh}$, dL/g[2] Amic Acid | Imide | $T_g$ ($T_m$), °C. Imide[4] | C-Imide[5] | Temp. of 5% Wt. Loss, °C. Imide[4] | C-Imide[5] |
| 1 | 9000 | 0.38 | 0.29[3] | 236 (323) | 243 | 489 | 516 |
| 1 | 5000 | 0.31 | 0.19[3] | 211 (268, 329) | 237 | 508 | 513 |
| 2 | 9000 | 0.47 | 0.43 | 232 (277) | 256 | 493 | 515 |
| 3 | 9000 | 0.43 | 0.38 | 239 | 263 | 487 | 521 |
| 3 | 6000 | 0.32 | 0.33 | 220 | 267 | 505 | 528 |
| 3 | 5000 | 0.29 | 0.28 | 221 | 250 | 513 | 512 |
| 4 | 9000 | 0.49 | 0.36[3] | 225 (323) | 264 | 486 | 494 |
| 5 | 9000 | 0.53 | — | 216 (273, 323) | 246 | 487 | 502 |
| 6 | 5000 | 0.27 | 0.28[3] | 208 (288) | 249 | 505 | 503 |
| 7 | 1500 | 0.16 | — | 262 (341) | 276 | 451 | 470 |

1. imide-1: ODPA/3,4'-ODA/PEPA
imide-2: 3:1 ODPA:BPDA/3,4'-ODA/PEPA
imide-3: 1:1 ODPA:BPDA/3'-ODA/PEPA
imide-4: 1:3 ODPA:BPDA/3,4'-ODA/PEPA
imide-5: ODPA/3,4'-ODA/PEPOPA
imide-6: BPDA/(.85)3,4'-ODA:(.15)APB/PEPA
imide-7: BTDA/3:1 3,4'-ODA:APB/PEPA
2. Inherent viscosity determined on 0.5% (w/v) NMP solution at 25° C.
3. Inherent viscosity determined on 0.5% (w/v) m-cresol solution at 25° C.
4. $T_g$ and $T_m$ of as-isolated oligomers (imide) by DSC at a heating rate of 20° C./min
5. Powdered samples after hold at 350° C./1 h/static air, C-imide: cured imide powder

TABLE 2

| | | | | | | |
|---|---|---|---|---|---|---|
| \multicolumn{7}{c}{UNORIENTED THIN FILM TENSILE PROPERTIES} |
| Imide[1] | Calc'd ($M_n$) g/mol | $T_g$, °C.[2] | Test Temp., °C. | Strength, ksi | Elongation at Modulus, ksi | Break, % |
| 1 | 9000 | 251 | 23 | 17.3 | 413 | 38 |
| | | | 177 | 9.4 | 318 | 60 |
| 1 | 5000 | 258 | 23 | 15.5 | 463 | 5 |
| | | | 177 | 9.3 | 313 | 17 |

TABLE 2-continued

UNORIENTED THIN FILM TENSILE PROPERTIES

| Imide[1] | Calc'd ($M_n$) g/mol | $T_g$, °C.[2] | Test Temp., °C. | Strength, ksi | Modulus, ksi | Elongation at Break, % |
|---|---|---|---|---|---|---|
| 2 | 9000 | 259 | 23 | 17.1 | 421 | 38 |
|   |      |     | 177 | 10.0 | 338 | 38 |
| 3 | 9000 | 262 | 23 | 20.2 | 431 | 69 |
|   |      |     | 177 | 10.7 | 341 | 70 |
| 3 | 6000 | 268 | 23 | 17.9 | 427 | 40 |
|   |      |     | 177 | 10.8 | 344 | 63 |
| 3 | 5000 | 267 | 23 | 19.2 | 430 | 40 |
|   |      |     | 177 | 10.4 | 315 | 56 |
| 4 | 9000 | 272 | 23 | 17.8 | 452 | 41 |
|   |      |     | 177 | 11.5 | 343 | 35 |
| 5 | 9000 | 247 | 23 | 16.9 | 408 | 35 |
|   |      |     | 177 | 8.6  | 293 | 56 |
| 6 | 5000 | 270 | 23 | 18.8 | 455 | 32 |
|   |      |     | 177 | 12.2 | 332 | 83 |
| 7 | 1500 | 274 | 23 | 15.3 | 407 | 5 |

1. Imide-1: ODPA/3,4'-ODA/PEPA
Imide-2: 3:1 ODPA:BPDA/3,4'-ODA/PEPA
Imide-3: 1:1 ODPA:BPDA/3,4'-ODA/PEPA
Imide-4: 1:3 ODPA:BPDA/3,4'-ODA/PEPA
Imide-5: ODPA/3,4'-ODA/PEPOPA
Imide-6: BPDA/(.85)3,4'-ODA:(.15)APB/PEPA
Imide-7: BTDA/3:1 3,4'-ODA:APB/PEPA
2. Determined by DSC at 20° C./min on film samples cured at 100, 225, 350° C. for 1 h each in flowing air.

TABLE 3

PRELIMINARY Ti-to-Ti TENSILE SHEAR PROPERTIES OF ODPA/3,4'-ODA/4-PEPA (CALCD($M$)$_n$ = 9000 g/mol)[1]

| Exposure | Test Temp., °C. | Strength psi | Cohesive Failure, % |
|---|---|---|---|
| Control | 23 | 7100 | 100 |
|  | 177 | 4300 | 100 |
| Jet Fuel[2] | 23 | 7200 | 95 |
|  | 177 | 4500 | 90 |
| Hydraulic Fluid[2] | 23 | 7300 | 95 |
|  | 177 | 4400 | 75 |
| Water Boil[2] | 23 | 6600 | 85 |
|  | 177 | 3400 | 55 |
| 1000 h/177° C./air[4] | 23 | 7100 | 90 |
|  | 177 | 4800 | 90 |
| 5000 h/177° C./air | 23 | 5600 | 55 |
|  | 177 | 4650 | 85 |

1. 1 h at 350° C./ 100 psi, tape~1% volatiles
2. Unstressed samples soaked in solvent for 72 h at ambient temperature
3. Unstressed samples boiled in water for 72 h
4. Unstressed samples aged in flowing air

TABLE 4

PRELIMINARY COMPOSITE PROPERTIES OF ODPA/3,4'-ODA/4-PEPA (CALCD ($M$)$_n$ = 9000 g/mol)*

| Property | Layup | Test Temp., °C. | Value |
|---|---|---|---|
| Flexural Strength, ksi | Unidirectional | 23 | 310 |
|  |  | 177 | 180 |
| Flexural Modulus, msi | Unidirectional | 23 | 20.4 |
|  |  | 177 | 18.1 |
| Short Beam Shear Strength, ksi | Unidirectional | 23 | 16.4 |
|  |  | 177 | 7.6 |
| Compressive Strength, ksi | Unidirectional | 23 | 187 |

*Composite cured 1 h at 350° C./200 psi, solution coated IM-7 carbon graphite fibers, fiber volume fraction ~66% with <1% void content

We claim:

1. A controlled molecular weight imide oligomer terminated with phenylethynyl phthalimide consisting of repeat units having the general structural formula

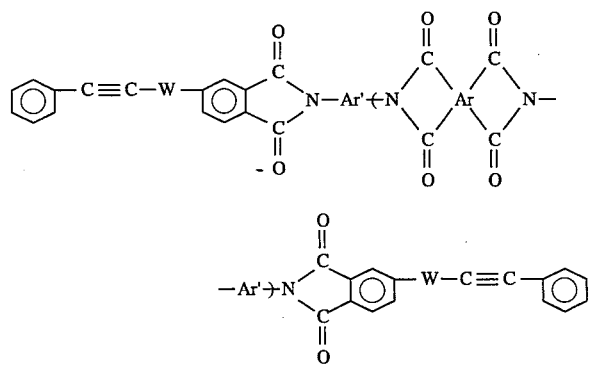

wherein Ar' is a radical selected from the group consisting of

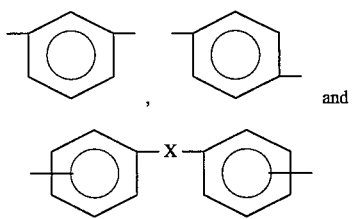

wherein the catenation is selected from the group consisting of 2,2';2,3';2,4'; 3,3';3,4' and 4,4', and X is a bond or X is a radical selected from the group consisting of

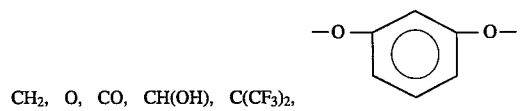

$CH_2$, O, CO, CH(OH), $C(CF_3)_2$,

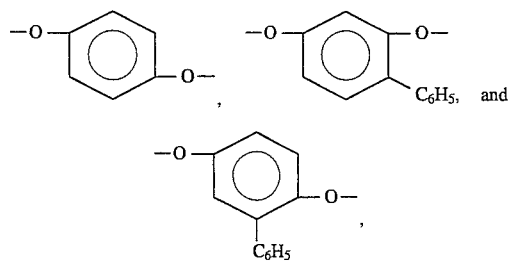

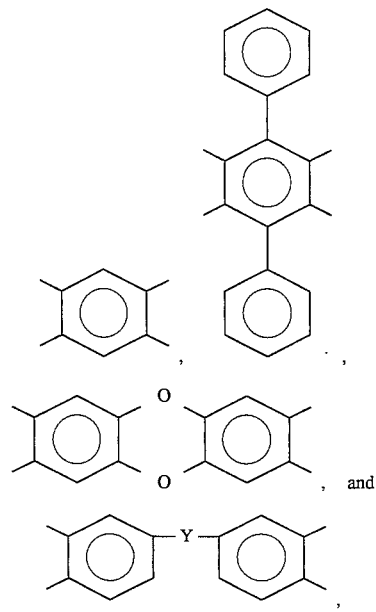

Wherein Ar is a radical selected from the group consisting of

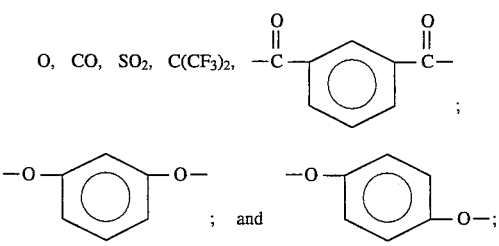

Wherein Y is a bond or Y is a radical selected from the group consisting of

O, CO, SO$_2$, C(CF$_3$)$_2$, 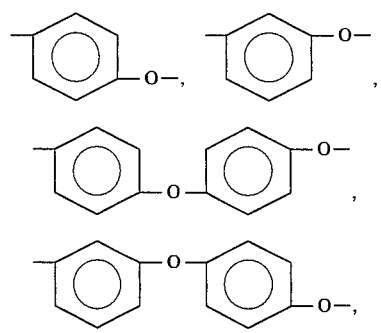

Wherein W is a bond or W is a radical selected from the group consisting of

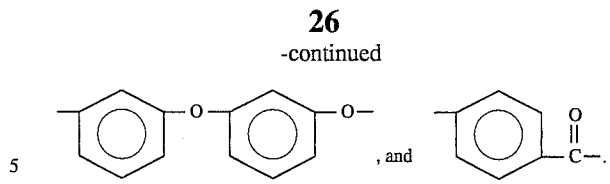

2. The controlled molecular weight phenylethynyl terminated imide oligomer of claim 1 wherein Ar' is a radical represented by

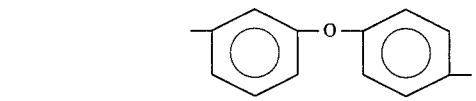

and Ar is a radical represented by

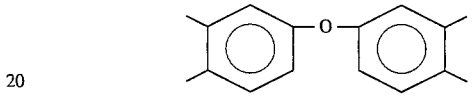

and W is a bond.

3. The controlled molecular weight phenylethynyl terminated imide oligomer of claim 1 wherein Ar' is a radical represented by

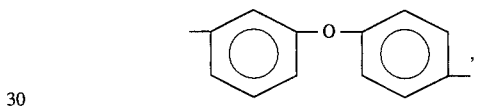

Ar is a radical represented by

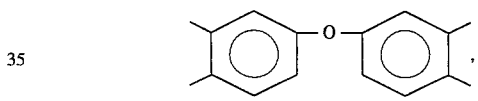

and W is a radical represented by

4. The controlled molecular weight phenylethynyl terminated imide oligomer of claim 1 wherein Ar' is a radical represented by

Ar is a radical represented by 0.5 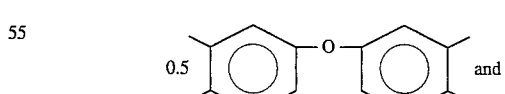 and 0.5 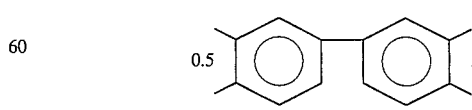, and W is a bond.

5. The controlled molecular weight phenylethynyl terminated imide oligomer of claim 1 wherein Ar' is a radical represented by

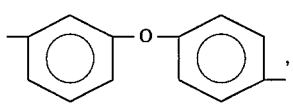

Ar is a radical represented by

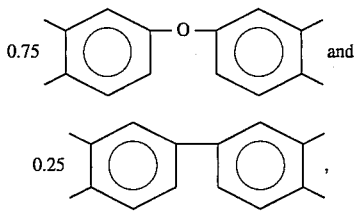

and W is a bond.

6. The controlled molecular weight phenylethynyl terminated imide oligomer of claim 1, wherein Ar' is a radical represented by

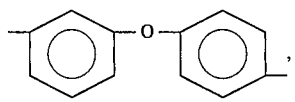

and Ar is a radical represented by

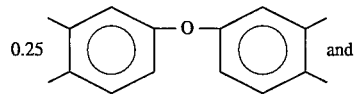

-continued

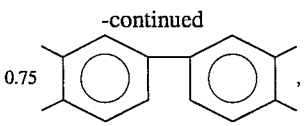

and W is a bond.

7. The controlled molecular weight phenylethynyl terminated imide oligomer of claim 1, wherein Ar' is a radical represented by

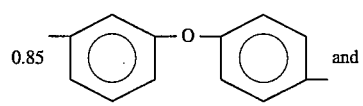

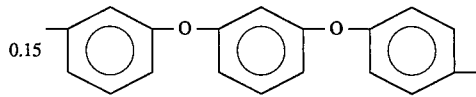

Ar is a radical represented by

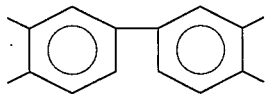

and W is a bond.

8. The controlled molecular weight phenylethynyl terminated imide oligomer of claim 1, wherein Ar' is a radical represented by

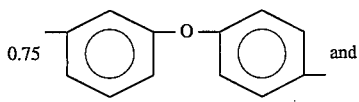

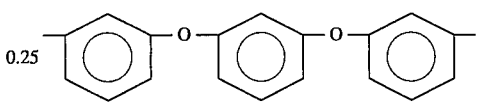

Ar is a radical represented by

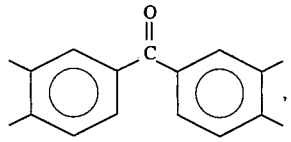

and W is a bond.

9. A phenylethynyl terminated amic acid oligomer having the general structural formula:

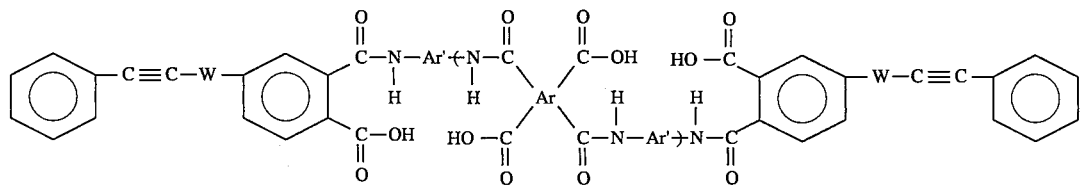

wherein Ar' is a radical selected from the group of

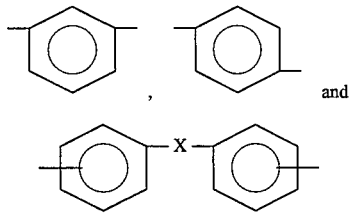

wherein the catenation is selected from the group consisting of 2,2';2,3';2,4'; 3,3';3,4' and 4,4' and X is a bond or X is a radical selected from the group consisting of $CH_2$, O, CO, CH(OH), $C(CF_3)_2$,

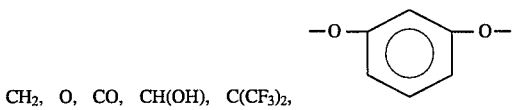

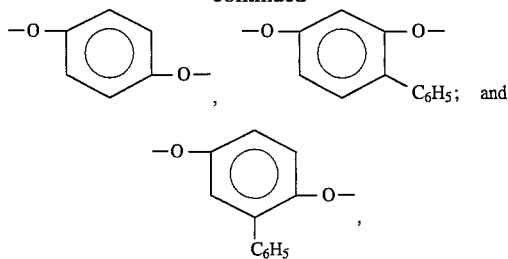

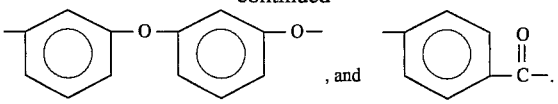

Wherein Ar is a radical selected from the group consisting of

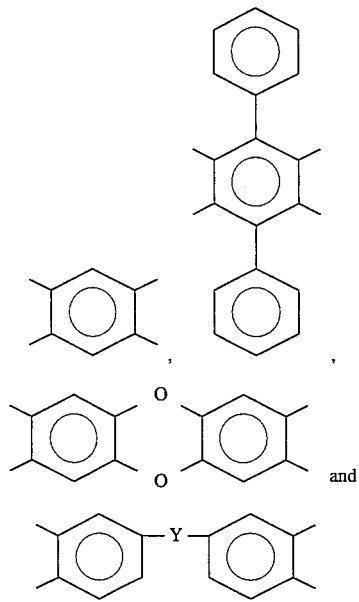

Wherein Y is a bond or Y is a radical selected from the group consisting of

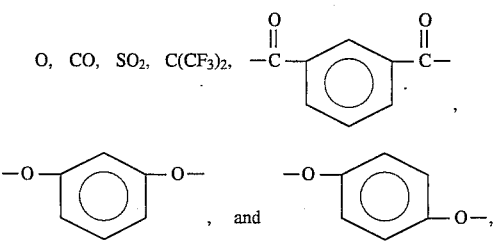

Wherein W is a bond or W is a radical selected from the group consisting of

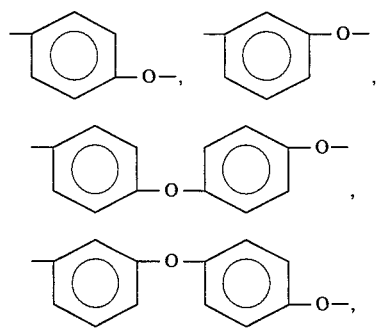

10. A controlled molecular weight amic acid oligomer terminated with phenylethynyl phthalamic acid according to claim 9, wherein Ar' is a radical represented by

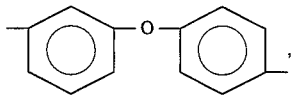

and Ar is a radical represented by

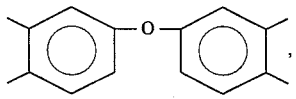

and W is a bond.

11. A controlled molecular weight amic acid oligomer terminated with phenylethynyl phthalamic acid according to claim 9, wherein Ar' is a radical represented by

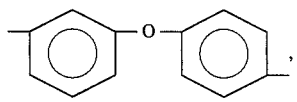

Ar is a radical represented by

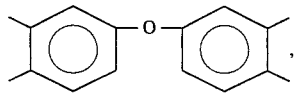

and W is a radical represented by

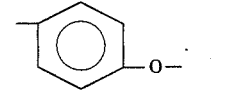

12. A controlled molecular weight amic acid oligomer terminated with phenylethynyl phthalamic acid according to claim 9, wherein Ar' is a radical represented by

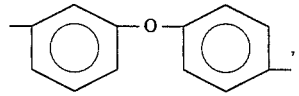

and Ar is a radical represented by

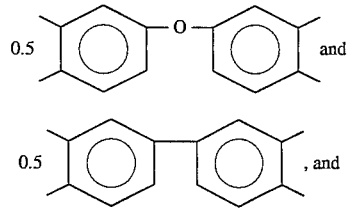

W is a bond.

13. A controlled molecular weight amic acid oligomer terminated with phenylethynyl phthalamic acid according to claim 9, wherein Ar' is a radical represented by

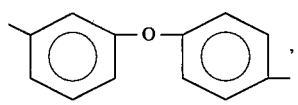

Ar is a radical represented by

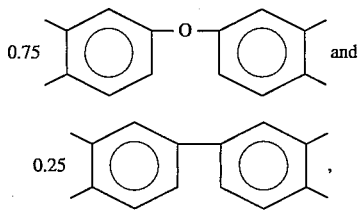

and W is a bond.

14. A controlled molecular weight amic acid oligomer terminated with phenylethynyl phthalamic acid according to claim 9, Ar' is a radical represented by

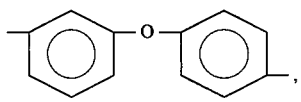

Ar is a radical represented by

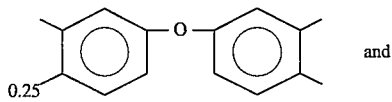

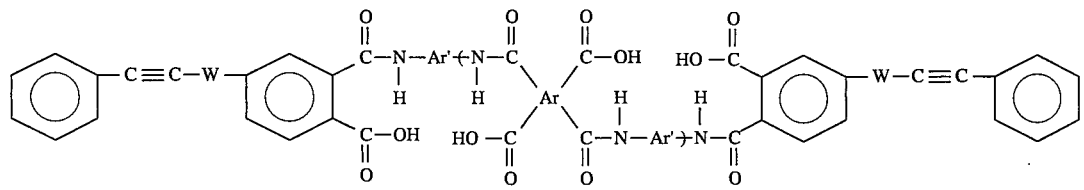

-continued

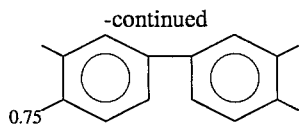

and W is a bond.

15. A process for synthesizing controlled molecular weight imide oligomers terminated with phenylethynyl phthalimide and having the general structural formula

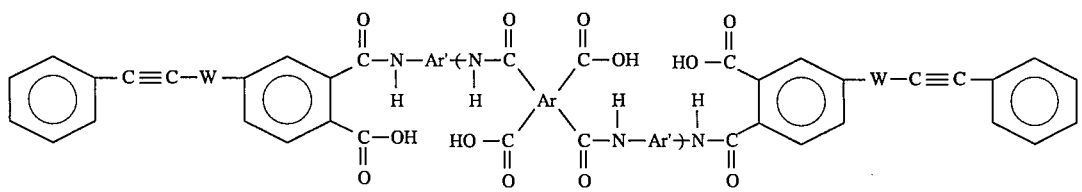

which process comprises cyclodehydrating precursor amic acid oligomers terminated with phenylethynyl phthalamic acid and having the general structural formula wherein the cyclodehydrating reaction is carried out in a polar aprotic solvent such as N,N-dimethylacetamide, N-methyl-2-pyrrolidinone, N-cyclohexyl- 2-pyrrolidinone, m-cresol, and dimethylsulfoxide; wherein the cyclodehydrating reaction is carried out with the application of heat and in the presence of a member selected from the group consisting of glacial acetic acid, isoquinoline, toluene, and xylene.

16. A process according to claim 15, wherein the cyclodehydrating is carried out employing acetic anhydride.

17. A process according to claim 15, wherein phenylethynyl terminated amic aid oligomers having the general structural formula are prepared by reacting an excess of a diamine with a dianhydride and phenylethynyl phthalic anhydride.

18. A process for synthesizing controlled molecular weight imide oligomers terminated with phenylethynyl phthalimide, according to claim 15 which process comprises reacting an amino terminated imide oligomer with phenylethynyl phthalic anhydride to form a phenylethynyl amic acid terminated imide oligomer, wherein the reaction is carried out in a polar aprotic solvent selected from the group consisting of N,N-dimethylacetamide, N-methyl-2-pyrrolidinone, N-cyclohexyl-2-pyrrolidinone, m-cresol, and dimethylsulfoxide; and wherein the reaction is carried out with the application of heat, followed by cyclodehydration of the phenylethynyl amic acid terminated imide oligomer.

19. A process according to claim 18, wherein cyclodehydration is carried out in a polar aprotic solvent selected from the group consisting of N,N-dimethylacetamide, N-methyl-2-pyrrolidinone, N-cyclohexyl-2-pyrrolidinone, m-cresol, and dimethylsulfoxide; and wherein the reaction is carried out with the application of heat; and wherein the reaction is carried out in the presence of a member selected from the group consisting of glacial acetic acid, isoquinoline, toluene, and xylene, and wherein the reaction is carried out in the presence of acetic arthydride.

20. A process for synthesizing controlled molecular weight imide oligomers terminated with phenylethynyl phthalimide, according to claim 15 which comprises reacting a diester derivative of a dianhydride and the ester derivative of phenylethynyl phthalic anhydride with an excess of a diamine.

21. A process according to claim 20, wherein the reaction is carried out in an alcohol solvent selected from the group consisting of methanol, ethanol, isopropanol, and phenol, and wherein the reaction is carried out with the application of heat.

22. A cured film prepared from a controlled molecular weight imide oligomer terminated with phenylethynyl phthalimide according to claim 1.

23. A cured film cast from a solution of a phenylethynyl terminated amic acid oligomer of claim 9, wherein the solution comprises a polar aprotic solvent selected from the group consisting of N,N-dimethylacetamide, N-methyl-2-pyrrolidinone, N-cyclohexyl-2-pyrrolidinone, m-cresol, and dimethylsulfoxide, and the film is thermally cured in air or in an inert atmosphere.

24. A cured film according to claim 23 which is prepared by compression molding of powders under heat and pressure.

25. A cured neat resin molding prepared from a controlled molecular weight imide oligomer terminated with phenylethynyl phthalimide according to claim 1.

26. A cured neat resin molding according to claim 25 which is prepared under heat and pressure.

27. A cured adhesive prepared from a controlled molecular weight imide oligomer terminated with phenylethynyl phthalimide according to claim 1.

28. A cured adhesive according to claim 27, which is prepared under heat and pressure.

29. A composite prepared from a controlled molecular weight imide oligomer terminated with phenylethynyl phthalimide according to claim 1.

* * * * *